United States Patent [19]

Shields

[11] Patent Number: 4,825,076

[45] Date of Patent: Apr. 25, 1989

[54] INFRA-RED SPECTROPHOTOMETRIC APPARATUS

[76] Inventor: John Shields, 23 North Lane, Wheldrake Nr. York, England

[21] Appl. No.: 60,996

[22] Filed: Jun. 9, 1987

Related U.S. Application Data

[63] Continuation-in-part of Ser. No. 796,910, Nov. 12, 1985, abandoned.

[30] Foreign Application Priority Data

Nov. 13, 1984 [GB] United Kingdom ............... 8428660
Apr. 17, 1985 [GB] United Kingdom ............... 8509875

[51] Int. Cl.$^4$ ............................................. G01N 21/35
[52] U.S. Cl. ................................. 250/343; 250/351; 250/353
[58] Field of Search ............... 250/351, 343, 339, 353, 250/373; 356/436, 437, 440

[56] References Cited

U.S. PATENT DOCUMENTS

| | | | |
|---|---|---|---|
| 3,281,597 | 10/1966 | Greenburg | 250/343 |
| 4,050,823 | 9/1977 | Frankenberger | 250/343 |
| 4,207,469 | 6/1980 | Hopkins et al. | 250/343 |
| 4,236,075 | 11/1980 | Nexo et al. | 250/343 |
| 4,310,763 | 1/1982 | Shields | 250/339 |
| 4,577,970 | 3/1986 | Meserol | 356/436 |
| 4,678,914 | 7/1987 | Melrose et al. | 250/343 |

FOREIGN PATENT DOCUMENTS

1000070 11/1976 Canada .............................. 250/343

Primary Examiner—Carolyn E. Fields
Attorney, Agent, or Firm—Barnes, Kisselle, Raisch, Choate, Whittemore & Hulbert

[57] ABSTRACT

An optical cell and detector assembly for a spectrophotometric analyzing apparatus which comprises a sample cell having walls of optically transparent material defining a sample cavity having closely adjacent the sample cavity a radiation detector and adjacent an opposite wall a lens whereby to focus radiation passing through the cell onto the detector. The apparatus may also comprise optical means for focussing the beam onto the sample cell, chopper means for periodically obscuring the beam, and filter means for selecting one or more wavelengths from the beam. The sample under test is an aqueous emulsion and the filters are chosen to determine the concentration of the non aqueous components of the emulsion by measuring the water displaced by the components.

8 Claims, 4 Drawing Sheets

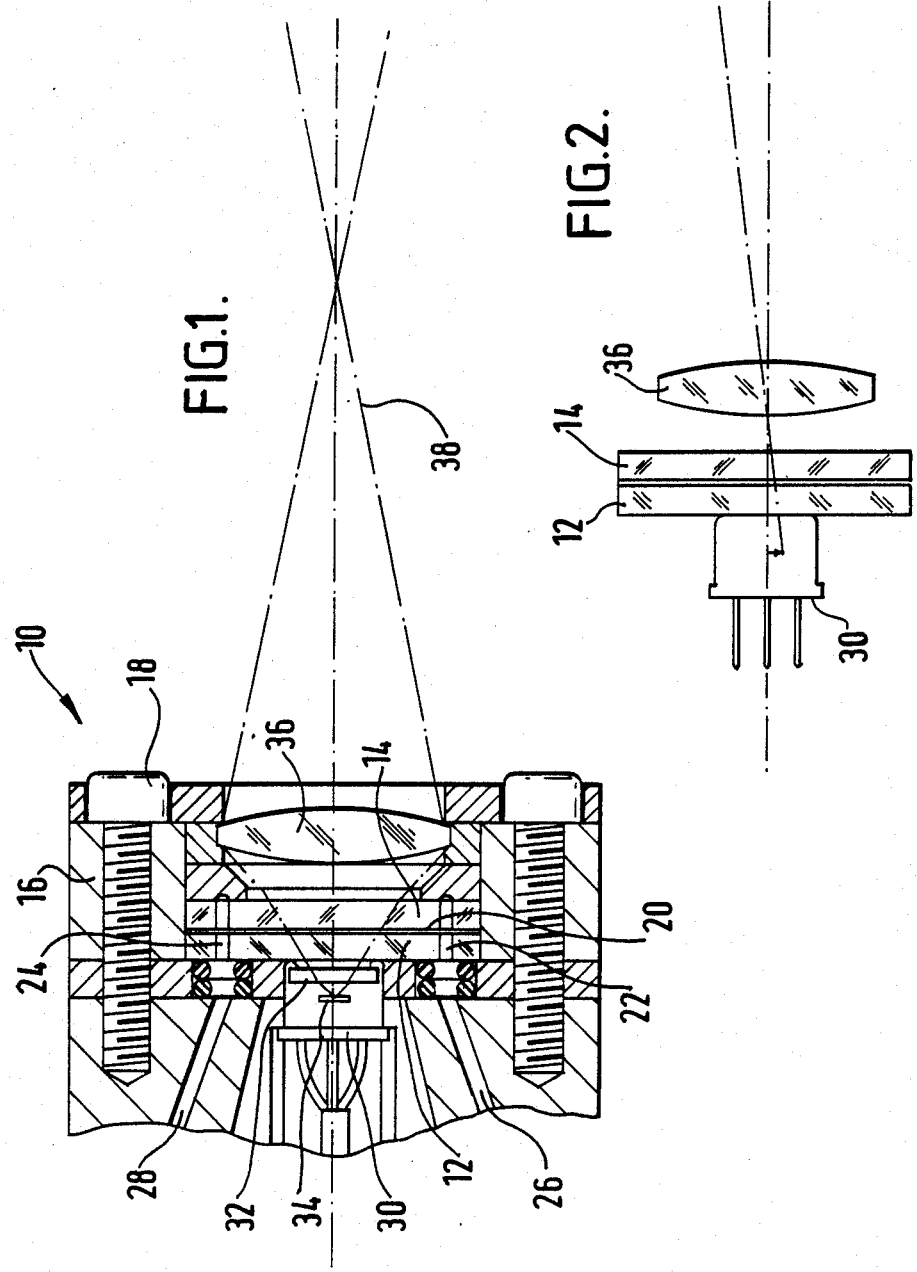

INFRA-RED SPECTROPHOTOMETRIC APPARATUS

This application is a continuation-in-part of application Ser. No. 796,910 filed Nov. 12, 1985 and now abandoned.

This invention relates to infrared spectrophotometric analysis apparatus and more particularly relates to a detector assembly therefor.

Infrared spectrophotometric analysers are employed for the analysis of emulsions and suspensions, for example in the dairy industry for analysing the fat, protein and lactose content in milk and milk products. An example of such apparatus is described in U.S. Pat. No. 4,310,763. In particular, FIG. 1 of this patent illustrates the optical lay-out of one form of such apparatus known as the "Multispec" instrument.

In this apparatus two beams of infrared light, each of a different wavelength are led alternately through an optical cell containing the sample under test to an ellipsoidal mirror from where it is focussed on to an infrared detector. The signal from the detector can be analysed in acordance with well known technology in this field to give a reliable estimate of the component being analysed for in the sample.

The above instrument, using the so-called 'double-beam-in-wavelength' system, analyses milk for fat, protein and lactose, and requires filters of suitable wavelength for each component, together with reference filters for each sample wavelength. Furthermore, a null-balance system is usually employed, involving a relatively expensive attenuator comb and associated servo mechanism and electronics.

Various factors affect the performance of such apparatus. For example, the presence of water vapour in the optical path of the apparatus causes interference by selectively absorbing part of the infrared signal. Thus, as well as attempting to reduce the water vapour within the apparatus, for reasons of conserving energy, optical path lengths should be kept to a minimum. Furthermore, the presence of large globules in the emulsion or suspension under test scatters infrared radiation, thus causing errors in the optical measurements of the components in the milk sample. As the amount of radiation scatter is proportional to the globule diameter, it is necessary to force the sample through a high pressure homogeniser to break down the globules. The necessity for homogenisation of, for example, milk samples greatly increases the cost of a suitable analysing instrument. Ellipsoidal mirrors are relatively expensive pieces of equipment, and the use of these tends to increase the cost of the instrument.

There is a great need for analysing apparatus which is inexpensive and yet has sufficient accuracy to be useful in dairy industries.

The invention seeks to provide economic apparatus for analysing samples which overcomes or reduces the above disadvantages.

In accordance with one aspect of the present invention there is provided an optical cell and detector assembly for a spectrophotometric analysing apparatus which comprises a sample cell having walls of optically transparent material defining a sample cavity having closely adjacent the sample cavity a radiation detector and adjacent an opposite wall a lens whereby to focus radiation passing through the cell on to the detector.

According to a second aspect of the present invention there is provided an infrared spectrophotometric analysing apparatus which comprises an infrared source and a detector therefor, optical means for focussing the beam onto a sample cell, chopper means for periodically obscuring the beam, and filter means for selecting one or more wavelengths from the beam, characterised in that the sample under test is an aqueous emulsion and that the filters are chosen to determine the concentration of the non aqueous components of the emulsion by measuring the water displaced by the components.

Placing the detector closely adjacent, or indeed abutting, the sample cell reduces the path length of the radiation, allows the ellipsoidal mirror formerly used to be dispensed with, and, since the temperature of the cell is controlled (for example as described in U.S. Pat. No. 4,310,736), enables the detector temperature to be monitored and controlled also. In particular, the effect of scattering owing to large globules within the sample under test is very much reduced since even scattered light is likely to be collected by a detector so close to the sample and thus homogenisation of the sample under test may be reduced or eliminated entirely. The detector may even replace part or all of one cell wall.

The apparatus of the invention is particularly applicable to the analysis of milk and dairy products. The most important practical measures required here are the amounts of fat and of solids, non-fat (SNF) in the sample. In the apparatus of the invention, by using a 'fat' filter such as a 5.7 micron filter and a 'water' filter, e.g. at 8.64 or 4.7 microns, these parameters can be simply and accurately determined.

In one embodiment, the apparatus of the invention includes a microcomputer, small display and keypad, an optics unit, control electronics and a pump/homogeniser. The optics unit is straightforward, having an infrared source and detector at either end of each light path, with a chopper, filter and cell or cells in between. The chopper has an equal area of 'windows' and reflective areas; the speed of said chopper is variable and is controled by the microprocessor. The filter is located between the chopper and the cell.

Different filters may be employed in the apparatus by means of a rotating wheel, the filters being mounted thereon, which rotates so as to place the desired filter into position. The cell is connected to the pump-/homogeniser.

Within the optic unit infrared radiation is emitted from an infrared source. This radiation is incident upon a convex lens which focusses the beam onto a chopper which is driven by a motor. The chopper, with its equal number of reflective areas and windows, alternately transmits then blocks the beam at a rate dependant upon the chopping frequency. The transmitted beam, after having traversed a suitable filter, is then focussed by a second convex lens onto a sample cell the radiation transmitted thereby being incident upon an infrared detector. A resulting A.C. signal is obtained which is indicative of the absorption which has taken place within the cell.

The spectrometer operates by changing filters and taking readings with, say, a sample of milk in the cell and comparing these with readings taken, say, with a sample of water in the cell. The readings are a simple ratio of the transmission (absorbance) at one, two or more selected wavelengths of the sample and reference. At one time, ratio methods were too inaccurate owing to drift in the senstivity of the detectors, and null-balance methods have been favoured. However, recent improvements in detector technology enable the ratio method to be used herein with sufficient accuracy and great cost saving.

For each sample, the cell is filled by the pump-/homogeniser, each filter is moved into position in turn, and measurements are taken. From these measurements, the concentrations of components of interest in the sample, for example fat and SNF, or fat, protein and lactose, in milk, are then calculated and displayed. In order to perform this calculation, it is necessary to have some reference measurement. For this purpose a distilled water sample is put through from time to time. Since there is a microcomputer with on-board clock/calendar in this embodiment, the instrument may itself request a reference sample if one has not been forthcoming for some time. The frequency with which the reference sample is required is dependent upon the stability of temperature and humidity within the instrument.

However, before any measurements are made, it is necessary to convert the optical signal arriving at the detector into computable form. This is done in four stages:

(a) The detector 34 (FIGS. 1 and 4) produces a small electronic signal;

(b) A pre-amplifier 60 (FIG. 4) amplifies this to a convenient level;

(c) A programmable gain amplifier 62 under the control of the computer 64 compensates for different signal levels from different filters; and (d) A 12 bit analogue to digital converter 66 converts the signal to digital form at a rate in excess of 1000 1samples per second.

Conventionally a tuned filter and synchronous rectifier (lock-in amplifier) is used, coupled with a low pass filter, and the resultant DC signal is sampled by the computer. By sampling the AC signal and processing it in the computer there are fewer electronic components which clearly means increased reliability. The method also leads to a lower noise level (there are fewer noise generators), lower cost, and an ability to vary the chopping frequency with no hardware changes.

The signal is sampled for some time, and between one and two thousand data points are stored. These data are then filtered, using a finite impulse response digital filter with a narrow pass band at the chopping frequency, and the amplitude of the resulting signal is then proportional to the optical signal magnitude.

Alternatively, a fast Fourier transform may be done and the amplitude at the chopping frequency computed directly. Although fast fourier transforms are time consuming, in this case we require that only one point in the frequency domain be computed, and in certain circumstances this method may be faster than filtering and estimating the amplitude.

In either case, the method of ascertaining the optical signal magnitude is by digital signal processing carried out by the computer. In a typical method of operation, for example in the analysis of milk samples, the cell is filled with milk and readings taken at 5.7 microns and at 8.64 microns. Similar measurements will have already been made with distilled water in the cell.

The difference between the readings for milk and water at 5.7 microns gives a measure of the fat content of the milk sample. The difference between the milk and water readings at 8.64 microns gives a measure of the total solids in the milk. Consequently the difference between these two readings, i.e. total solids and fat, gives a value of the 'solids non-fat' of the milk. Other wavelengths of "water filter" can be employed, e.g. 4.7 microns, but we have found that 8.64 microns gives good results, with a standard deviation of less than 0.04%.

The fat and the SNF levels are by far the most important measures needed in the analysis of milk. The microprocessor within the embodiment is programmed to give a direct read-out of these two levels without the operator having to perform any calculations.

One embodiment of the invention has only two lenses and no ellipsoidal or concave mirrors in its optical system. Furthermore, owing to the cell and detector arrangement, a homogeniser may be dispensed with. Thus the cost of the apparatus of this embodiment is only a fraction of that of conventional analysers.

The spectrometer operates by changing filters and taking readings with say, a sample of milk in the sample cell and comparing these with similar readings with, say, a reference of water in the sample cell. A microprocessor may be incorporated as before to compare and integrate the readings automatically without greatly increasing the cost. The readings are a simple ratio of the transmission (absorbance) at one, two or more selected wavelengths of the sample and reference.

An advantageous form of this apparatus comprises only one cell. This may firstly be filled with distilled water and measurements taken at, say, 8.64 and 5.7 microns. The cell is then filled with a milk sample and the measurements repeated. Since the measurements on water may be stored by the instrument, there is no need to repeat the water measurements with each succeeding milk sample. Thus, a single beam at a single wavelength (at any one time) is passed through a single cell. This leads to savings in cost of the optical system needed as compared with double-beam instrument—without incurring penalties in speed of operation owing to the stored water reference information.

Instruments embodying either or both aspects of the invention may be made to any desired level of sophistication from very basic (and hence inexpensive), e.g. for use in developing countries, to multi-functional employing, for example, filters for protein and lactose as well as fat and having powerful computing facilities built in.

The invention will be described further, by way of example, with reference to the accompanying drawings, in which:

FIG. 1 is a partial sectional view of a cell and a detector assembly in accordance with the invention;

FIG. 2 is a simplified view corresponding to FIG. 1 and illustrating the optical path;

Figure 3:
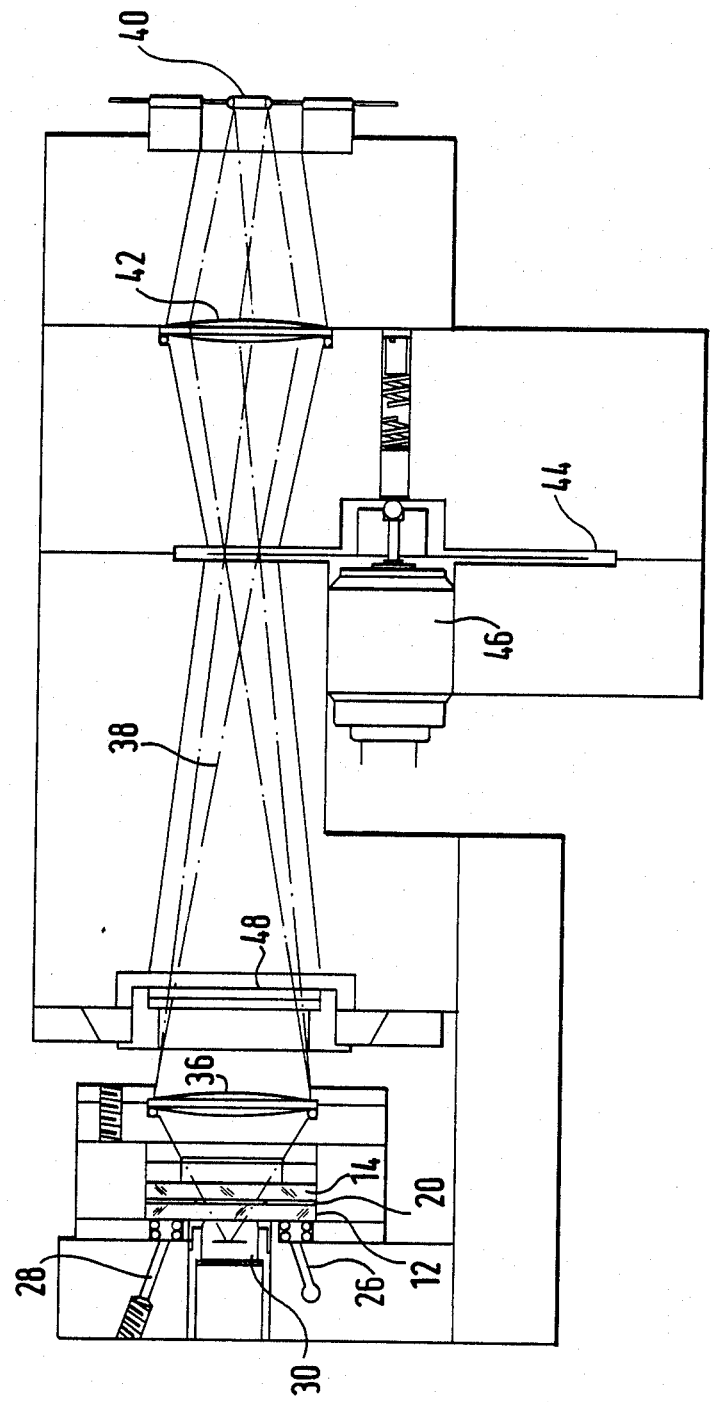
FIG. 3 is a spectrometer incorporating the cell and detector.

Referring to the drawings, and assembly generally designated 10 comprises a fair of cell walls 12, 14 of optically transparent material, which, for infrared analysis, could be silver iodide, calcium fluoride, germanium, zinc-sulphide, or potassium bromide. The cell walls 12, 14 are held within a body 16 by means of bolts 18 in a conventional manner and defined between them a sample cavity 20. The cavity 20 connects by passageways 22 and 24 to inlet and exit ports 26, 28 for fluid samples.

On one wall 12 of the cell where is mounted a radiation detector 30 having a radiation transparent window 32 and a detecting element 34.

Mounted adjacent to the opposite wall 14 of the cell is a lens 36 made of a similarly optical transparent material to that of the cell walls 14, 12. Radiation 38 of the appropriate wave length in, as described more fully hereinafter, directed on to the lens 36 from the remainder of the instrument.

The radiation 38 is focused by the lens 36 through the sample cell and detector window 32 on to the detector element 34. As shown in the drawings, the lens has a focal point at the detector element. The detector 30 is preferably of a type having a relatively large window 32, for example 10 mm diameter or even larger. This ensures that not only can the radiation 38 be focussed within the receiving area of the detecting element 34 but that the bulk of any light scattered within the cell will also be collected thus improving the sensitivity of the apparatus constructed in accordance with the invention. The ellipsoidal mirror is eliminated, and the associated optical path length also. Furthermore, since the body 16 is temperature controlled so as to control the temperature of the cell (as described in U.S. Pat. No. 4,310,763) the detector 30, being incorporated with the cell, is also temperature controlled, so that drift owing to temperature variations of the detector 30 is reduced or eliminated.

In operation, a reference sample is put in the cell and absorbs varying amounts of radiation at the different wavelengths selected by the filters, and these levels are recorded. Subsequent milk samples absorb more strongly than the water, and so the optical signal at the detector 30, which is an A.C. signal caused by the operation of the chopper, is of a different magnitude dependant upon concentration of components and the filters selected. By computation, estimates may be obtained, from the data so recorded, of the concentration of components of interest within the milk.

If desired other filters may be used to give information about protein and lactose. Cross-corrections for interferring components can be carried out using equations known per se and, where a microprocessor is used, these corrections can be programmed in.

Furthermore, the simplification embodied in the instrument of the invention enables it to be manufactured with very small dimensions. This in turn allows it to be incorporated in plant or equipment for process control.

In another embodiment, the detector may actually be incorporated into the cell replacing some or all of the cell exit wall 12.

Referring now to FIG. 3, the remainder of the optical system for a low-cost spectrometer is illustrated. An infrared source 40 is focussed by means of a lens (or lens group) 42 onto a chopper 14 which alternately allows the beam to pass and blocks it off at a frequency determined by the speed of its drive motor 46. If the detector 30 is a photon detector, a high chopper frequency (e.g. 200 c.p.s.) is preferred; but for slower operating detectors very much lower freqencies may be employed (e.g. 10-25 c.p.s.). The detector electronics are tuned to and governed by the chopper speed as known in the art. A replaceable filter 48 is placed between the chopper 44 and the lens 36.

In a typical method of operation, in the analysis of milk samples, the cell is firstly filled with water as a reference and the filter 48 is chosen at the Fat 'A' waveband, 5.7 microns. Measurements are taken with the beam 38 both on and blocked off (for a 'background' level). The filter 48 is then changed to a 'water filter' i.e. one which corresponds to high water absorption, e.g. 8.64 microns, and the readings repeated. This sequence is then repeated with a sample of milk in the cell.

The difference between the readings for milk and water at 5.7 microns (corrected for background) give a measure of the fat content of the milk sample. The difference between the milk and water readings at 8.64 microns (corrected for background) give a measure of the total solids in the milk. Consequently the difference between total solids and fat gives the 'solids, non-fat' ('SNF') of the milk. The fat and SNF levels are by far the most important measures needed in the analysis of milk. A microprocessor within the apparatus can be programmed to give a direct read-out of these two levels without the operator having to perform any calculations.

Thus sufficiently accurate measurements of the most important parameters for milk analysis can be obtained with a extremely inexpensive instrument.

While the invention has been described in relation to instruments useful for analysing milk and dairy products, and the filters chosen have been of wavelengths appropriate to this end-use, it is not so-limited. Other aqueous emulsions can be analysed and filters will be chose accordingly. Even in the analysis of milk, the particular filter values described are not the only ones which can be used; for example, other filter wavelengths useful for the analysis of milk fat include 3.46 microns and 6.84 microns.

The invention described hereabove would be a valuable asset for the dairy industry as it provides a quick and reliable method of ascertaining the quality of milk samples at a relatively inexpensive price.

Figure 5:
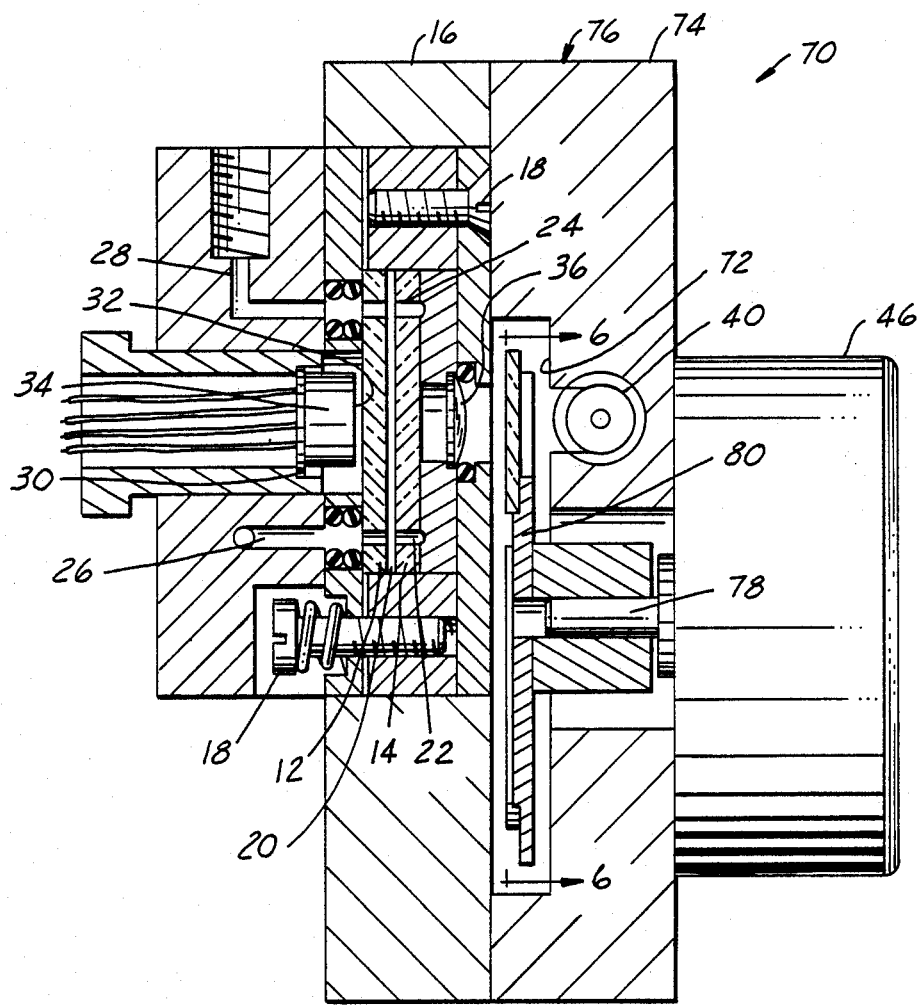
FIG. 5 is a sectional view of a compact spectrometer assembly in accordance with a modified embodiment of the invention.
Figure 6:
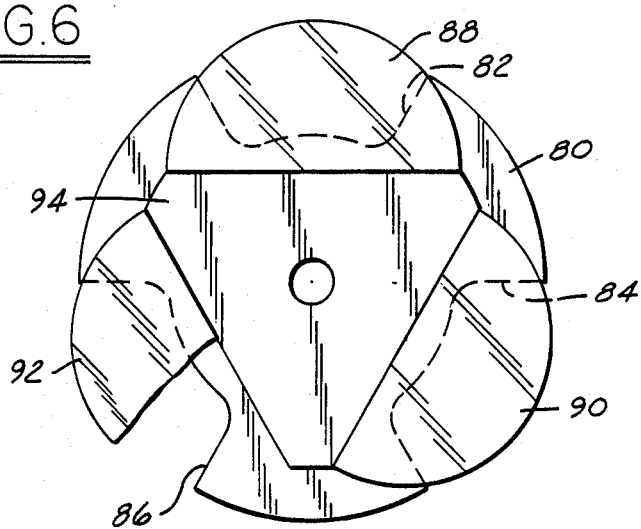
FIG. 6 is a fragmentary elevational view of the disc and filter wheel assembly taken substantially along the line 6—6 in FIG. 5.

FIGS. 5-6 illustrate a compact spectrometer 70 in accordance with a modified embodiment of the invention. Reference numerals identical to numerals hereinabove employed indicate correspondingly identical elements. In the spectrometer 70 of FIGS. 5-6, the light source or lamp 40 is mounted within a cavity 72 in a block 74 which is affixed (by means now shown) to block 16 to form an overall frame assembly 76. Lamp 40 is aligned axially with detector 34, the sample cell formed between windows 12,14 and focusing lens 36. Infrared energy from lamp 40 in thus focused by lens 36 through the sample cell onto detector element 34 as hereinabove described. Chopper motor 46 is carried by block 74 externally of cavity 72 and has a shaft 78 parallel with the optical axis between detector 34 and lamp 40. A chopper disc 80 is mounted to shaft 78 within cavity 72 such that its periphery passes between lamp 40 and lens 36 as chopper disc 80 and shaft 78 are rotated by motor 46. A series of arcuate apertures, specifically three apertures 82,84,86, are formed in the periphery of disc 80 so as to alternately transmit light from lamp 40 to lens 36 when an aperture 82,84 or 86 is positioned between the lamp and lens, and to block such transmission when a disc segment between the apertures is positioned between the lamp and lens, disc 80 being constructed of optically opaque material.

Figure 4:
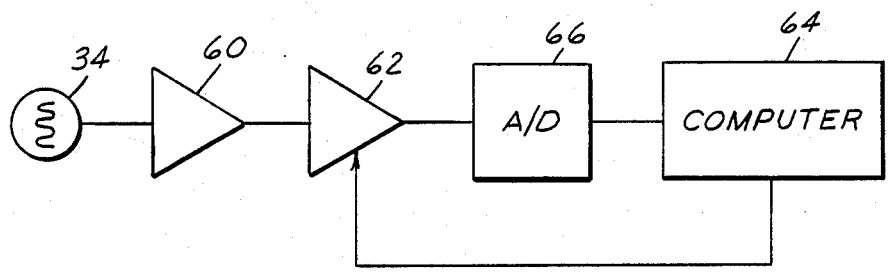
FIG. 4 is a schematic diagram of apparatus electronics.
Figure 7:
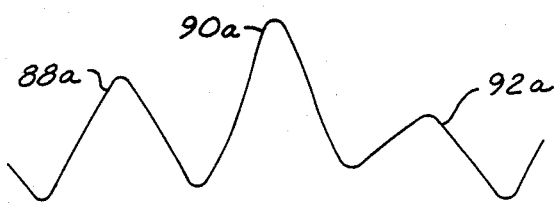
FIG. 7 is a fragmentary schematic illustration of cell output in the embodiment of FIGS. 5–6.

Infrared filters 88,90,92 are carried by disc 80 covering each aperture 82,84,86 respectively. In the embodiment of the invention illustrated in the drawings, filters 88-92 are of semi-circular construction, being seated against a triangular hub 94 centrally of disc 80 so that the body of each filter covers a corresponding aperture. Each filter 88,90,92 has an infrared transmission characteristic corresponding to a preselected infrared wavelength for spectrophotometric analysis of a sample contained in the cavity between cell windows 12,14. For example, filter 88 may transmit energy in a narrow band centering about the wavelength of 5.7 μm, filter 90 may transmit energy centered at a wavelength of 3.46 μm, and filter 92 may transmit energy centered about a wavelength of 8.64 μm. Energy is thus received at detector 34 in a pattern exemplified in FIG. 7 having an a.c. component corresponding to angular velocity of motor 46 and disc 80, and with the intensity of transmission through each filter 88-92 and the amplitide 88a,90a,92a of the detector output corresponding to a preselected characteristic of the liquid sample contained in the test cell. Such intensity amplitudes are fed to computer 64 (FIG. 4) for analysis in any conventional manner.

The embodiment of FIGS. 5-6 thus provides a compact and inexpensive spectrometer in which the volume and expense associated with complex folding mirrors, filter wheels and the like have been eliminated. The light beam is completely contained, so that effects of dust and/or humidity are greatly reduced. The temperature of the entire assembly may be closely controlled above ambient in the manner disclosed in U.S. Pat. No. 4,310,763. As presently envisioned, computer 64 (FIG. 4) may be programmed to distinguish between signal peaks 88a,90a and 92a, and between the corresponding wavelengths of filters 88,90,92, without synchronization with disc 80. However, if required, disc 80 may be provided with a suitable synchronization aperture, and a corresponding signal provided to computer 64 for distinguishing between the filters and corresponding signal intensities.

I claim:

1. An infrared spectrometer for measuring optical characteristics of aqueous emulsions containing light-scattering particles comprising a sample cell for receiving and containing an aqueous emulsion for test, means including a source for generating infrared energy at preselected wavelengths, an infrared detector, means for focusing energy from said source through the cell onto said detector, and means responsive to energy incident on said detector for indicating a preselected characteristic of an aqueous emulsion in said cell,
    characterized in that said cell, said focusing means and said detector comprise a unitary assembly in which said cell includes means forming a pair of opposed spaced-apart parallel transparent windows carried by a frame and defining a sample cavity therebetween, in which said detector is externally mounted within said frame adjacent to one of said windows and contains a detector element spaced from and external to said cavity, and in which said focusing means comprises a focusing lens positioned within said frame externally adjacent to the other of said widows externally of said cavity and constructed to focus said energy convergently through said windows and cavity onto said detector element, said lens having a focal point at said element externally of said cavity.

2. An infrared spectrometer as claimed in claim 1 further characterized in that said means responsive to energy incident on said detector comprises means for amplifying output from the detector, means for compensating for different signal levels at differing ones of said wavelengths, and an analogue-to-digital converter to convert the signal to digital form for computing.

3. The spectrometer set forth in claim 1 wherein said source comprises a lamp carried in said unitary assembly by said frame, and filter means carried within said frame between said source and said detector for obtaining infrared energy through said cell at said preselected wavelengths onto said detector.

4. The spectrometer set forth in claim 3 further comprising chopper means including a motor carried by said frame, and a chopper disc positioned between said lamp and said detector and coupled to said motor for alternately transmitting and blocking light energy from said source to said detector.

5. The spectrometer set forth in claim 4 wherein said chopper disc comprises an opaque disc having at least one aperture in the periphery thereof, and wherein said filter means comprises an infrared filter carried by said disc over said at least one aperture.

6. The spectrometer set forth in claim 5 wherein said disc has a plurality of apertures in the periphery thereof, and wherein said filter means comprises a plurality of infrared filters carried by said discover respective ones of said apertures and having differing preselected infrared transmission characteristics corresponding to differing said preselected wavelengths.

7. The spectrometer set forth in claim 6 wherein said detector, said cell, said lens and said lamp are carried in coaxial alignment by said frame, and wherein said disc is positioned with its periphery disposed between said lamp and said lens to rotate about an axis parallel to such axis of alignment.

8. An infrared spectrometer for measuring optical characteristics of materials comprising a sample cell for receiving and containing a test sample of material, a source of infrared radiation, an infrared detector, means for focusing energy from said source through said cell onto said detector, means responsive to energy incident on said detector for indicating a preselected characteristic of said material, filter means including at least one infrared filter element and means for placing said element between said source and said detector, and chopper means for alternately permitting and interrupting transmission of light energy from said source and to said detector,
    characterized in that said chopper means and said filter means together comprise an opaque disc having a plurality of apertures in the periphery thereof, said filter means comprising a plurality of infrared filter elements carried by said disc over respective ones of said apertures and having differing preselected infrared transmission characteristics, and a motor coupled to said disc for continuously rotating said disc,
    said cell, said focusing means, said detector, said chopper means, said filter means and said source comprising a unitary assembly in which said cell includes means forming a pair of opposed spaced-apart parallel transparent windows carried by a frame and defining a sample cavity therebetween, and in which said detector is externally mounted within said frame adjacent to one of said windows and contains a detector element spaced from and external to said cavity.

* * * * *